US012714303B2

(12) United States Patent
Nakajima et al.

(10) Patent No.: US 12,714,303 B2
(45) Date of Patent: Aug. 25, 2026

(54) MYOPIA PROGRESSION ANALYSIS DEVICE, MYOPIA PROGRESSION ANALYSIS SYSTEM, MYOPIA PROGRESSION ANALYSIS METHOD, AND MYOPIA PROGRESSION ANALYSIS PROGRAM

(71) Applicant: TOPCON CORPORATION, Tokyo (JP)

(72) Inventors: Masashi Nakajima, Tokyo (JP); Yasufumi Fukuma, Wako (JP); Shu-Yun Yeh, Tokyo (JP)

(73) Assignee: TOPCON CORPORATION, Itabashi-ku (JP)

(*) Notice: Subject to any disclaimer, the term of this patent is extended or adjusted under 35 U.S.C. 154(b) by 697 days.

(21) Appl. No.: 18/248,373

(22) PCT Filed: Oct. 11, 2021

(86) PCT No.: PCT/JP2021/037549
§ 371 (c)(1),
(2) Date: Apr. 7, 2023

(87) PCT Pub. No.: WO2022/080307
PCT Pub. Date: Apr. 21, 2022

(65) Prior Publication Data

US 2023/0404390 A1 Dec. 21, 2023

(30) Foreign Application Priority Data

Oct. 12, 2020 (JP) ................................ 2020-172224

(51) Int. Cl.
*A61B 3/10* (2006.01)
*A61B 3/103* (2006.01)
*A61B 5/00* (2006.01)

(52) U.S. Cl.
CPC ............ *A61B 3/1005* (2013.01); *A61B 3/103* (2013.01); *A61B 5/4842* (2013.01)

(58) Field of Classification Search
CPC ....... A61B 3/028; A61B 3/1005; A61B 3/103; A61B 5/4842; G02C 2202/24
See application file for complete search history.

(56) References Cited

U.S. PATENT DOCUMENTS

2017/0209036 A1* 7/2017 Brennan ................ G02C 7/027
2018/0160894 A1* 6/2018 Gupta .................. A61B 5/4842
2018/0228364 A1* 8/2018 Brennan ................ G02C 7/028

FOREIGN PATENT DOCUMENTS

CN 107358036 A 11/2017
CN 111329442 A 6/2020
(Continued)

OTHER PUBLICATIONS

Cheung et al., "Validity of axial length measurements for monitoring myopic progression in orthokeratology," IOVS, Mar. 2013, vol. 54, No. 3, 1613-1615. (Year: 2013).*
(Continued)

*Primary Examiner* — Nicholas R. Pasko
(74) *Attorney, Agent, or Firm* — Chiesa Shahinian & Giantomasi PC

(57) ABSTRACT

Disclosed is a myopia progression analysis device including: an eye axial length acquisition section that acquires an eye axial length of an eye of a subject; a reference value acquisition section that acquires a numerical value related to a physical characteristic of the subject other than the eye axial length as a reference value; a relative eye axial length calculator that calculates a relative eye axial length through relativization of the eye axial length acquired by the eye axial length acquisition section using the reference value acquired by the reference value acquisition section; a population information acquisition section that acquires popula- (Continued)

tion information which is a set of information about relative eye axial lengths of a plurality of comparison targets to be compared with the subject; and a relative position information calculator.

8 Claims, 6 Drawing Sheets

(56) References Cited

FOREIGN PATENT DOCUMENTS

| | | | | |
|---|---|---|---|---|
| JP | 2004-238804 | A | | 8/2004 |
| JP | 5667730 | B1 | | 2/2015 |
| JP | 2019170706 | A | * | 10/2019 |
| KR | 10-2020-0077085 | A | | 6/2020 |
| WO | 2021/123455 | A2 | | 6/2021 |

OTHER PUBLICATIONS

English machine translation of JP 2019170706 A. (Year: 2019).*

Rusnak et al., "Myopia Progression Risk: Seasonal and Lifestyle Variations in Axial Length Growth in Czech Children," Journal of Ophthalmology, vol. 2018, https://doi.org/10.1155/2018/5076454. (Year: 2018).*

Hyman et al., "Relationship of age, sex, and ethnicity with myopia progression and axial elongation in the correction of myopia evaluation trial," Arch Ophthalmol, vol. 123, Jul. 2005, 977-987, doi: 10.1001/archopht.123.7.977. (Year: 2005).*

International Search Report and Written Opinion mailed Dec. 14, 2021, in connection with International Patent Application No. PCT/JP2021/037549, 10 pgs (including translation).

* cited by examiner

MYOPIA PROGRESSION ANALYSIS DEVICE, MYOPIA PROGRESSION ANALYSIS SYSTEM, MYOPIA PROGRESSION ANALYSIS METHOD, AND MYOPIA PROGRESSION ANALYSIS PROGRAM

CROSS-REFERENCE TO RELATED APPLICATIONS

This application is a National Stage under 35 U.S.C. 371 of International Patent Application No. PCT/JP2021/037549, filed Oct. 11, 2021, which claims priority from Japanese Patent Application No. 2020-172224, filed Oct. 12, 2020; the disclosures of all of which are incorporated herein by reference in its entirety.

TECHNICAL FIELD

The present disclosure relates to a myopia progression analysis device, a myopia progression analysis system, a myopia progression analysis method, and a myopia progression analysis program.

BACKGROUND ART

Myopia can cause blindness, and thus it is important to check the progression of myopia. Myopia is classified into axial myopia and refractive myopia. Measuring an eye axial length to check the current eye axial length allows checking of the progression of axial myopia, and treatment or correction is performed based on the progression.

An ophthalmologic information processing program disclosed in Patent Document 1 has been known as an example. It is disclosed in this example that whether the eyes of a subject have axial myopia is determined based on a measurement value of refractive power acquired by refractive power measurement by an analyzer, one or more measurement values of an intraocular distance acquired by an intraocular distance measurement section, information about the subject, and standard data.

CITATION LIST

Patent Document

PATENT DOCUMENT 1: Japanese Unexamined Patent Publication No. 2004-238804

SUMMARY OF THE INVENTION

Technical Problems

However, an absolute value of the eye axial length alone is insufficient for the check of the progression of axial myopia. Physical characteristics vary among individuals, and human beings with large bodies tend to have large eyeballs. Thus, an individual cannot be determined to have axial myopia solely based on a high absolute value of the eye axial length. Thus, it is difficult to accurately check the progression of axial myopia based on the absolute value of the eye axial length alone.

An object of the present disclosure is to provide a myopia progression analysis device, a myopia progression analysis system, a myopia progression analysis method, and a myopia progression analysis program that can exclude the influence of individual growth and allow accurate check of the progression of axial myopia.

Solution to the Problems

To achieve the above-described object, the disclosed myopia progression analysis device includes: an eye axial length acquisition section that acquires an eye axial length of an eye of a subject; a reference value acquisition section that acquires a numerical value related to a physical characteristic of the subject other than the eye axial length as a reference value; a relative eye axial length calculator that calculates a relative eye axial length through relativization of the eye axial length acquired by the eye axial length acquisition section using the reference value acquired by the reference value acquisition section; a population information acquisition section that acquires population information which is a set of information about relative eye axial lengths of a plurality of comparison targets to be compared with the subject; and a relative position information calculator that compares the relative eye axial length of the subject calculated by the relative eye axial length calculator with the relative eye axial lengths of the plurality of comparison targets included in the population information to calculate relative position information indicating a relative position of the relative eye axial length of the subject in the set of comparison targets.

To achieve the above-described object, the disclosed myopia progression analysis system includes: a measurement section that measures an eye axial length of an eye of a subject; an eye axial length acquisition section that acquires the eye axial length measured by the measurement section; a reference value acquisition section that acquires a numerical value related to a physical characteristic of the subject other than the eye axial length as a reference value; a relative eye axial length calculator that calculates a relative eye axial length through relativization of the eye axial length acquired by the eye axial length acquisition section using the reference value acquired by the reference value acquisition section; a population information acquisition section that acquires population information which is a set of information about relative eye axial lengths of a plurality of comparison targets to be compared with the subject; and a relative position information calculator that compares the relative eye axial length of the subject calculated by the relative eye axial length calculator with the relative axial lengths of the plurality of comparison targets included in the population information to calculate relative position information indicating a relative position of the relative eye axial length of the subject in the set of comparison targets.

To achieve the above-described object, the disclosed myopia progression analysis method includes: acquiring, by an eye axial length acquisition section, an eye axial length of an eye of a subject; acquiring, by a reference value acquisition section, a numerical value related to a physical characteristic of the subject other than the eye axial length as a reference value; calculating, by a relative eye axial length calculator, a relative eye axial length through relativization of the eye axial length acquired by the eye axial length acquisition section using the reference value acquired by the reference value acquisition section; acquiring, by a population information acquisition section, population information which is a set of information about relative eye axial lengths of a plurality of comparison targets to be compared with the subject; and comparing, by a relative position information calculator, the relative eye axial length of the subject calculated by the relative eye axial length calculator with the relative eye axial lengths of the plurality of comparison targets included in the population information to calculate relative position information indicating a relative position of the relative eye axial length of the subject in the set of comparison targets.

To achieve the above-described object, the disclosed myopia progression analysis program causes a computer to execute: acquiring, by an eye axial length acquisition section, an eye axial length of an eye of a subject; acquiring, by a reference value acquisition section, a numerical value related to a physical characteristic of the subject other than the eye axial length as a reference value; calculating, by a relative eye axial length calculator, a relative eye axial length through relativization of the eye axial length acquired by the eye axial length acquisition section using the reference value acquired by the reference value acquisition section; acquiring, by a population information acquisition section, population information which is a set of information about relative eye axial lengths of a plurality of comparison targets to be compared with the subject; and comparing, by a relative position information calculator, the relative eye axial length of the subject calculated by the relative eye axial length calculator with the relative eye axial lengths of the plurality of comparison targets included in the population information to calculate relative position information indicating a relative position of the relative eye axial length of the subject in the set of comparison targets.

Advantages of the Invention

The present disclosure can exclude the influence of individual growth and allows accurate check of the progression of axial myopia.

DETAILED DESCRIPTION

System Configuration

Figure 1:
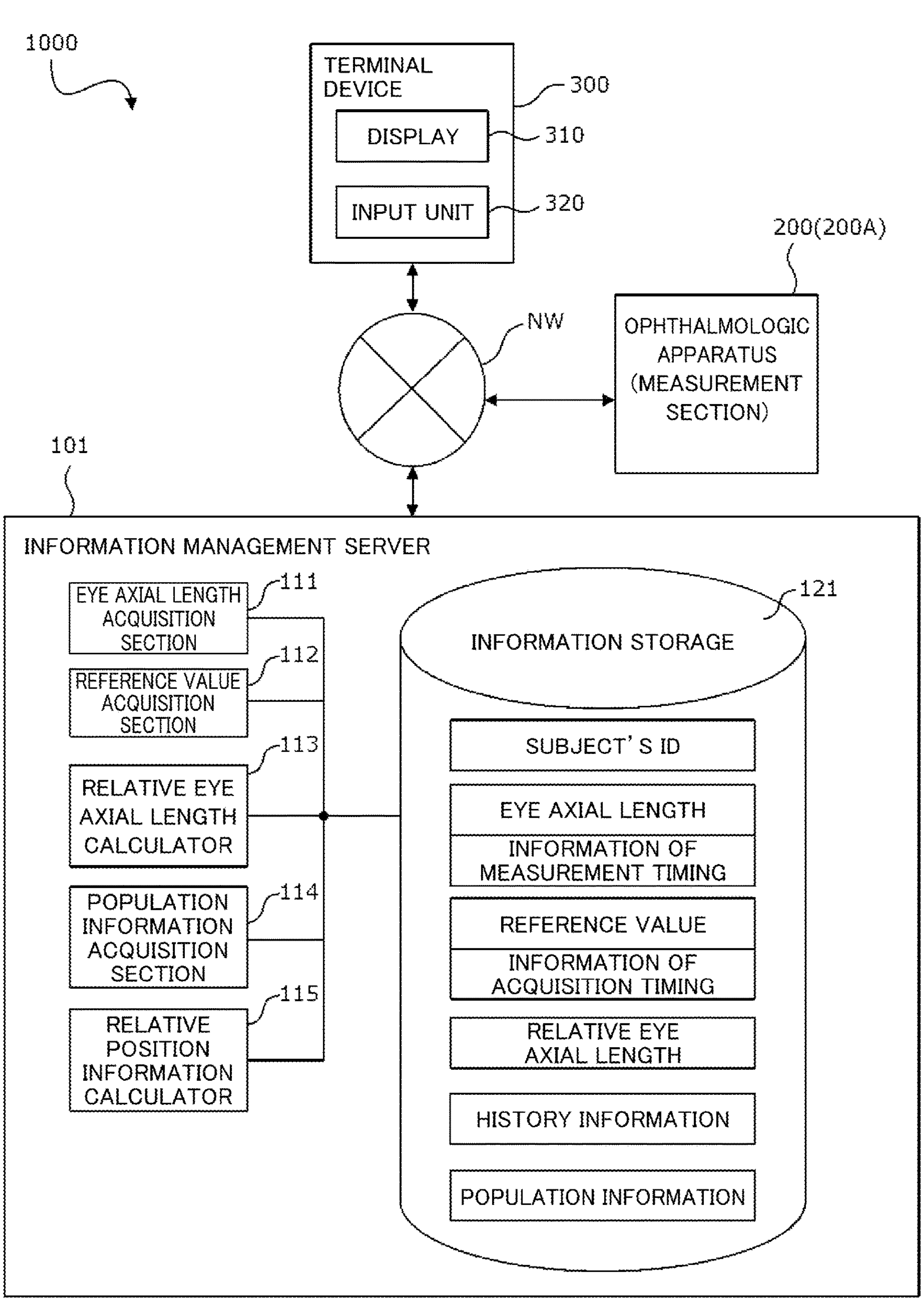
FIG. 1 is a system configuration diagram of a myopia progression analysis system of an embodiment of the present disclosure.

Embodiments of the present disclosure will be described below with reference to the drawings. FIG. 1 is a system configuration diagram illustrating a myopia progression analysis device including an information management server 101 of the embodiment of the present disclosure, i.e., a myopia progression analysis system 1000. This drawing shows a configuration example in which the information management server 101, an ophthalmologic apparatus 200, and a terminal device 300 are different apparatuses and are connected to each other via a network NW. Note that the myopia progression analysis system 1000 provided may be a stand alone system including all the components integrated together. In the myopia progression analysis system 1000, the ophthalmologic apparatus 200 functions as a measurement section 200A for measuring an eye axial length and a reference value indicating physical characteristics related to the eye. As will be described later, it may be proposed a myopia progression analysis device that can externally acquire the eye axial length of a subject and the reference value for relativization of the eye axial length and can store these values, and thus requires no ophthalmologic apparatus 200.

In the myopia progression analysis system 1000 shown in FIG. 1, the information management server 101 and the terminal device 300 handled by a user are communicatively connected via the network NW. The network NW is, for example, the Internet or a virtual private network (VPN). Although FIG. 1 shows the terminal device 300 alone that is supposed to be handled by a single user for the sake of simple illustration, the information management server 101 can be connected to two or more terminal devices, i.e., two or more users, via the network NW. A single terminal device may be handled by two or more users.

The myopia progression analysis system 1000 is mainly used by an ophthalmologist or any other specialist to analyze the progression of myopia of the subject and give appropriate treatments or correction depending on the progression. An operating company of the myopia progression analysis system 1000 provides, by using the system, services that support the treatments by the ophthalmologist. The operating company can provide the services to a plurality of ophthalmologists. The information management server 101 of the myopia progression analysis system 1000 is managed by the operating company and proposed for the ophthalmologists to use the terminal device 300 and the ophthalmologic apparatus 200. Note that the ophthalmologists may manage the system by themselves using the information management server 101. An apparatus for acquiring the eye axial length and the eye-related reference value used for relativization of the eye axial length, which will be described later, may have a measurement function similar to that of the ophthalmologic apparatus 200, and may be installed in places other than ophthalmologic hospitals, such as a glasses store.

The terminal device 300 is a device such as a personal computer (PC), a smartphone, a tablet PC, or a mobile phone. The terminal device 300 may access the information management server 101 via dedicated application software installed in the terminal device. In addition, the terminal device 300 may access the information management server 101 using an operating environment (e.g., an application programming interface (API), a cloud service, or a platform) provided by the information management server 101.

An input unit 320 is, for example, a device that is handled by a user to input and select information, such as a keyboard, a mouse, a trackball, or a touchpad. The input unit 320 may be a touch screen integrated with a display 310 of a smartphone, a tablet, or a liquid crystal display or organic EL display of a PC. The input unit 320 may be a voice input device.

The display 310 is a device that shows information to the user. The display 310 may be a device independent of the terminal device 300 or may be a device such as a liquid crystal display or organic EL display of a smartphone or a tablet.

The ophthalmologic apparatus 200 is mainly used to acquire the eye axial length of the subject and the reference value related to the physical characteristics of the subject, which will be described later. Although the ophthalmologic apparatus 200 is not always necessary as long as the eye axial length of the subject and the reference values related to the physical characteristics of the subject are externally acquired, the ophthalmologic apparatus 200 has the capability of measuring the eye axial length and other reference values, and thus is able to acquire the eye axial length and the physical characteristics of the subject, allowing quick analysis of the progression of myopia. The ophthalmologic apparatus 200 can also acquire the characteristics of the eyeballs of the subject simultaneously with the eye axial length, allowing smooth analysis of the progression of myopia.

Figure 2:
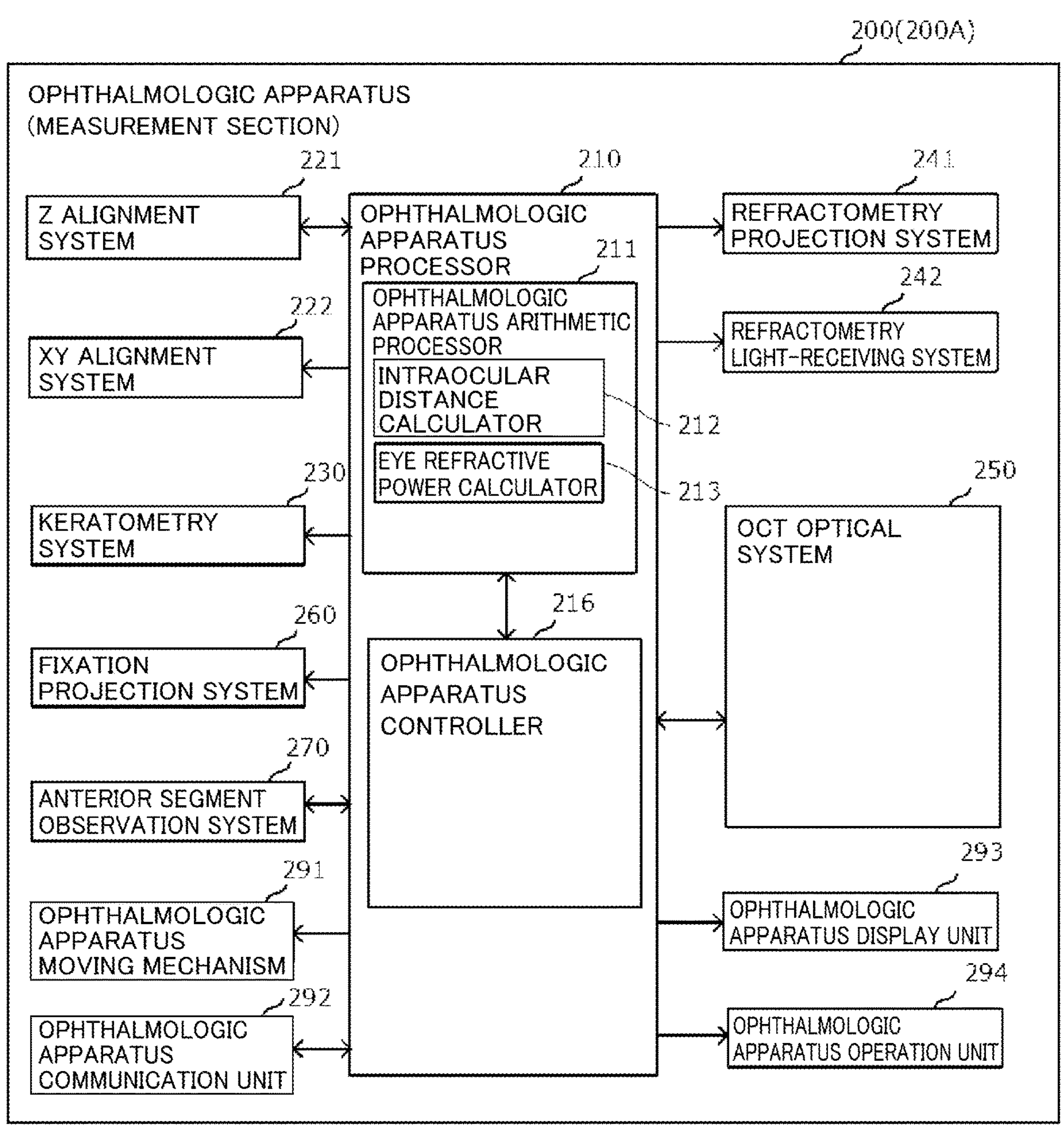
FIG. 2 is a diagram showing a configuration of an ophthalmologic apparatus.

The ophthalmologic apparatus 200 can measure a plurality of items such as the eye axial length, pupillary distance, corneal curvature, corneal diameter, and dioptric power of the subject's eye. These items are measured mainly by the functions of the ophthalmologic apparatus as a refractive power measurement device (reflectometer) and as an optical interference eye axial length measurement device using optical coherence tomography (OCT). FIG. 2 shows a configuration of the ophthalmologic apparatus 200. The ophthalmologic apparatus 200 includes an ophthalmologic apparatus processor 210, an ophthalmologic apparatus arithmetic processor 211, an intraocular distance calculator 212, an eye refractive power calculator 213, an ophthalmologic apparatus controller 216, a Z alignment system 221, an XY alignment system 222, a keratometry system 230, a refractometry projection system 241, a refractometry light-receiving system 242, an OCT optical system 250, a fixation photographing system 260, an anterior segment observation system 270, an ophthalmologic apparatus moving mechanism 291, an ophthalmologic apparatus communication unit 292, an ophthalmologic apparatus display unit 293, and an ophthalmologic apparatus operation unit 294. Note that components and details that are less relevant to the function of the myopia progression analysis system 1000 of the present disclosure will not be described below.

The intraocular distance calculator 212 analyzes the result of detection of interfering light by the OCT optical system 250 to specify peak positions of the detection result of the interfering light corresponding to a predetermined site in the eye, and thus can obtain the eye axial length of the subject's eye based on the distance between the specified peak positions.

The eye refractive power calculator 213 can obtain values such as the dioptric power by analyzing a ring-shaped image (a pattern image) obtained when an imaging element of the refractometry light-receiving system 242 receives reflection of a ring-shaped luminous flux (a ring-shaped measurement pattern) projected on the fundus of the eye by the refractometry projection system 241.

The eye refractive power calculator 213 can obtain the corneal curvature and the corneal diameter by analyzing a kerato-ring image acquired by the anterior segment observation system 270.

The pupillary distance can be obtained by adding a difference between the positions of the pupil centers of the right and left eyes on images captured by the anterior segment observation system 270 and the amount of movement that the moving mechanism 291 has made when the images are captured.

The information management server 101 includes an eye axial length acquisition section 111, a reference value acquisition section 112, a relative eye axial length calculator 113, a population information acquisition section 114, a relative position information calculator 115, and an information storage 121.

The information storage 121 stores an ID of the subject and items of information associated with the ID, such the eye axial length, information about timing of eye axial length measurement, the reference value, information about timing of reference value acquisition, a relative eye axial length, history of each item of information, and population information.

The ID of the subject may be information indicating the name of the subject, the number of a health insurance card, or the number of a patient ID card unique to a hospital. The eye axial length may be information indicating the eye axial lengths of the left and right eyes of the subject or a mean value thereof. The information about measurement timing may indicate a measurement date including year, month, and day of the measurement of the eye axial length of the subject and time when the measurement was made on the measurement date.

The reference value may be a numerical value related to the physical characteristics of the subject other than the eye axial length and associated with the subject's ID. Specifically, the physical characteristics related to the eyes of the subject may be information indicating a pupillary distance, a corneal curvature, a corneal diameter, a dioptric power, measurement values of these items for each of the left and right eyes, or mean values thereof. Note that the corneal diameter and the corneal curvature well represent the physical characteristics of the eyes of each individual, and thus are suitable examples of the reference value. The physical characteristics of body parts of the subject other than the eyes may be information indicating an eye socket size, height, and head size of the subject. The physical characteristics of the body parts other than the eyes are also suitable examples of the reference value for excluding the influence of individual growth. The size may include a length, an area, and a volume measured at any position of those body parts. The size may be of any other body part than the above-described body parts. The information about acquisition timing may indicate an acquisition date including year, month, and day when these reference values were acquired and time when the acquisition was made on the acquisition date.

The relative eye axial length will be described later.

The population information indicates data related to the eye axial lengths, reference values, and relative eye axial lengths of a plurality of comparison targets basically other than the subject, timing to measure these values, and timing to acquire these values. The population information is normative data for checking the position of the relative eye axial length of the subject who is a target of analysis of the progression of myopia in a standard population. The population information may exclude information that allows identification of the subject, such as the subject's name, from the viewpoint of personal information protection. Data of the comparison targets included in the population information is not easy to obtain, and thus the number of the data may be appropriately set to the number that is statistically reliable for comparison. All the data does not need to be raw data and may be representative values obtained by statistical processing on the data of the comparison targets.

Myopia Progression Analysis Function

The myopia progression analysis function of the present disclosure will be described below with reference to the components.

The eye axial length acquisition section 111 has the function of acquiring the eye axial length of the subject through the measurement by the ophthalmologic apparatus 200, data input to the terminal device 300 via the input unit 320, and information collection via the network NW.

The reference value acquisition section 112 has the function of acquiring the reference value, which is a numerical value related to the physical characteristics of the subject other than the eye axial length, through the measurement by the ophthalmologic apparatus 200, data input to the terminal device 300 via the input unit 320, and information collection via the network NW. In particular, the reference value related to the subject's eye can be acquired from the measurement value of the ophthalmologic apparatus 200. Other physical characteristics related to the body parts of the subject other than the eyes can be acquired mainly by data input to the terminal device 300 via the input unit 320 and information collection via the network NW.

The relative eye axial length calculator 113 has the function of calculating a relative eye axial length through relativization of the eye axial length acquired by the eye axial length acquisition section 111 using the reference value acquired by the reference value acquisition section 112.

The relative eye axial length calculator 113 calculates a numerical value by, for example, dividing the eye axial length of the subject measured at predetermined measurement timing by the height of the subject, which is a reference value obtained at the same timing as the eye axial length measurement (eye axial length/height), or dividing the eye axial length by the corneal curvature obtained at the same timing as the axial length measurement (eye axial length/corneal curvature). In the calculation, the height or corneal curvature used as the denominator will never be zero. However, the reference value that takes a positive or negative value across zero such as the dioptric power is used as the numerator, and a numerical value obtained by dividing the dioptric power by the eye axial length (dioptric power/eye axial length) can be used as the relative eye axial length.

It is preferable that the timing of the eye axial length measurement and the timing of the reference value acquisition coincide with each other as much as possible, but they may be as close as possible. In particular, when one of eye-related physical characteristics other than the eye axial length is selected as the reference value and the ophthalmologic apparatus 200 acquires the physical characteristic simultaneously with the eye axial length, the timing of the eye axial length measurement coincides with the timing of the reference value acquisition, allowing calculation of a more reliable relative eye axial length.

If the relativization of the eye axial length is performed using both of a numerical value related to the physical characteristics of the subject's eye, such as the pupillary distance, corneal curvature, corneal diameter, or dioptric power of the subject, and a numerical value related to other physical characteristics such as the eye socket size, height, or head size of the subject, a relative eye axial length considering the physical characteristics more comprehensively can be calculated.

When the relative eye axial length is calculated through relativization of the eye axial length in this way, a normalized eye axial length taking the influence of the physical growth of the subject into account can be obtained. Specifically, a human being experiences great changes in body dimensions in infancy and a growth period, and it is not only the eye axial length that changes greatly, but also the pupillary distance, the corneal curvature, the corneal diameter, the dioptric power, the eye socket size, the height, and the head size. In such a situation, the eye axial length increases due to growth rather than abnormality. However, attention is required if the eye axial length significantly increases compared to the growth of the other body parts. When the relative eye axial length of the present disclosure is used as an index, the influence of the growth is canceled, allowing correct evaluation of the axial length. This leads to accurate prediction of axial myopia.

The population information acquisition section 114 has the function of acquiring population information which is a set of information about a plurality of relative eye axial lengths of comparison targets to be compared with the subject. As described above, the population information indicates data related to the eye axial lengths, reference values, and relative eye axial lengths of a plurality of targets basically other than the subject, timing to measure these values, and timing to acquire these values. The population information includes data necessary for calculating the relative eye axial length, for example, information about relative eye axial lengths for comparison calculated in advance.

The relative position information calculator 115 has the function of comparing the relative eye axial length of the subject calculated by the relative eye axial length calculator 113 with a plurality of relative eye axial lengths included in the population information to calculate relative position information indicating a relative position of the relative eye axial length of the subject in a set of subjects.

Figure 3:
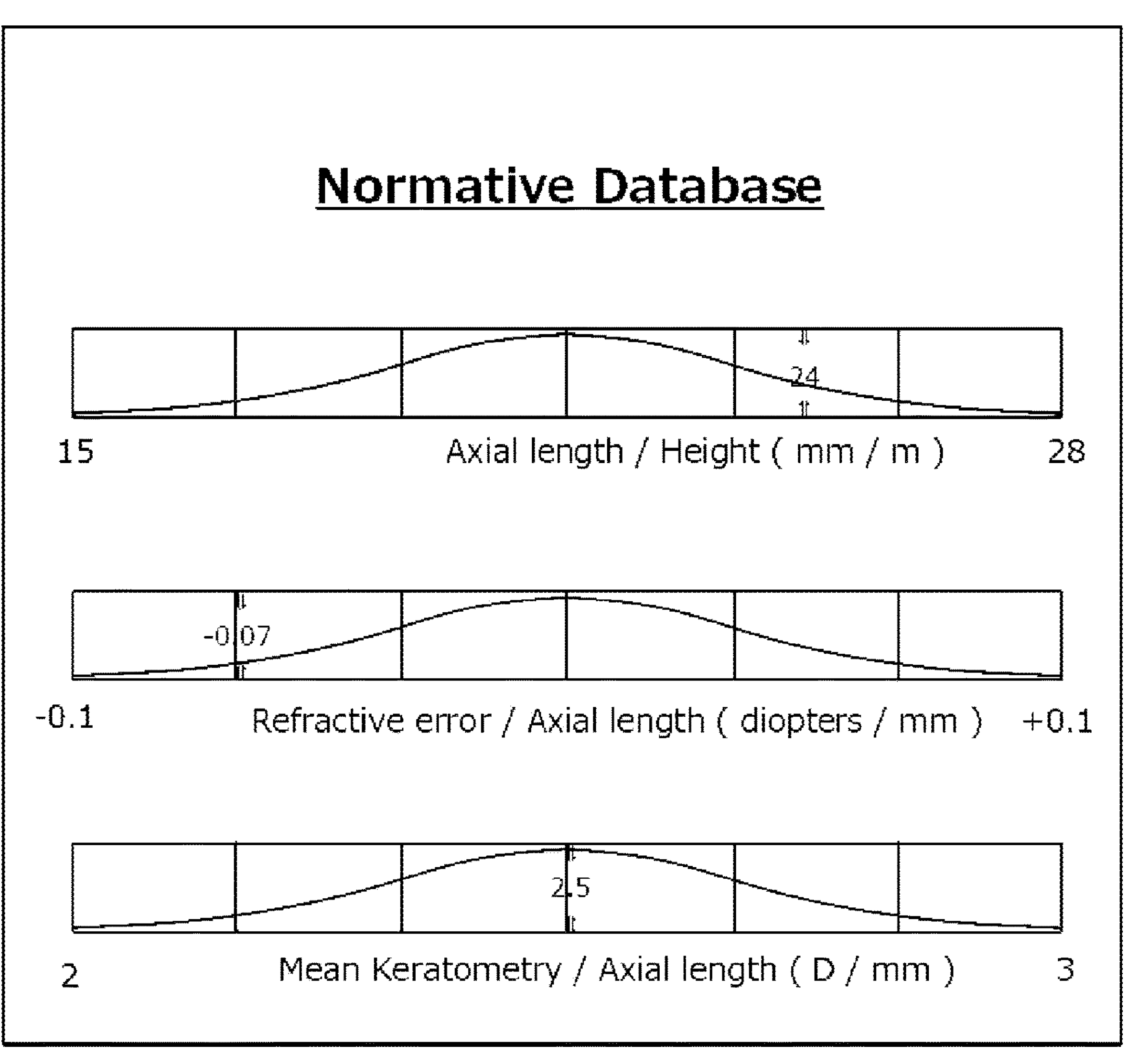
FIG. 3 shows an example of relative position information shown on a display of a terminal device.

FIG. 3 specifically shows the relative position information. FIG. 3 shows a screen that appears on the display 310 of the terminal device 300, for example. This screen shows the relative position of the relative eye axial length of the subject calculated by the relative position information calculator 115 in the set of comparison targets.

The screen of FIG. 3 shows three graphs of the relative eye axial length of a subject and its relative position. The top one of the three graphs will be described first. The horizontal axis of the graph indicates the relative eye axial length, i.e., the value of eye axial length/height (mm/m). The convex curve is a bell curve that evokes a normal distribution and is used to help understand the relative position, and does not necessarily represent a collection of data of population information. The five vertical lines passing through the graph represent positions of ±G with respect to the mean value. For example, the numerical value of the relative eye axial length of this subject is 24 in this graph, which lies relatively between $+\sigma$ and $+2\sigma$ with respect to the mean value of the population for comparison. This position is easy to understand.

In the middle graph, the horizontal axis indicates the relative eye axial length, i.e., the value of dioptric power/eye axial length (diopters/mm). For example, the relative eye axial length of this subject is −0.07 in this graph, which lies relatively between $-\sigma$ and $-2\sigma$ with respect to the mean value of the population for comparison. This position is easy to understand. Likewise, the bottom graph indicates the relative eye axial length, which is the value of mean keratometry/axial length (D/mm), i.e., the value of mean corneal curvature/eye axial length. For example, the relative eye axial length of this subject is 2.5 in this graph, which is close to the mean value of the population for comparison. This position is easy to understand.

As described above, the relative position information calculator 115 can calculate the relative position information indicating the position of the relative eye axial length of the subject in the population. The relative position information calculator 115 can calculate not only the relative position of one relative eye axial length, but also the relative positions of a plurality of relative eye axial lengths, allowing analysis of the progression of myopia in a more versatile manner.

The relative position information calculator 115 has the function of calculating, using the information about the measurement timing associated with the eye axial length which is a basis for the calculation of the relative eye axial length and the information about the acquisition timing associated with the reference value indicating the physical characteristics, the relative position information showing the relative eye axial length at timing when the timing of the eye axial length measurement corresponds to the timing of the acquirement of the reference value indicating the physical characteristics on a time-series basis and the relative eye axial lengths included in the population in chronological order.

The relative position information calculator 115 has the function of comparing each of the relative eye axial lengths measured at the different timings with a set of a plurality of relative eye axial lengths included in the population information by using two or more relative eye axial lengths of one subject measured at different timings, to calculate relative position information showing the relative position of the relative eye axial length of the subject in a set of subjects in chronological order.

Figure 4:
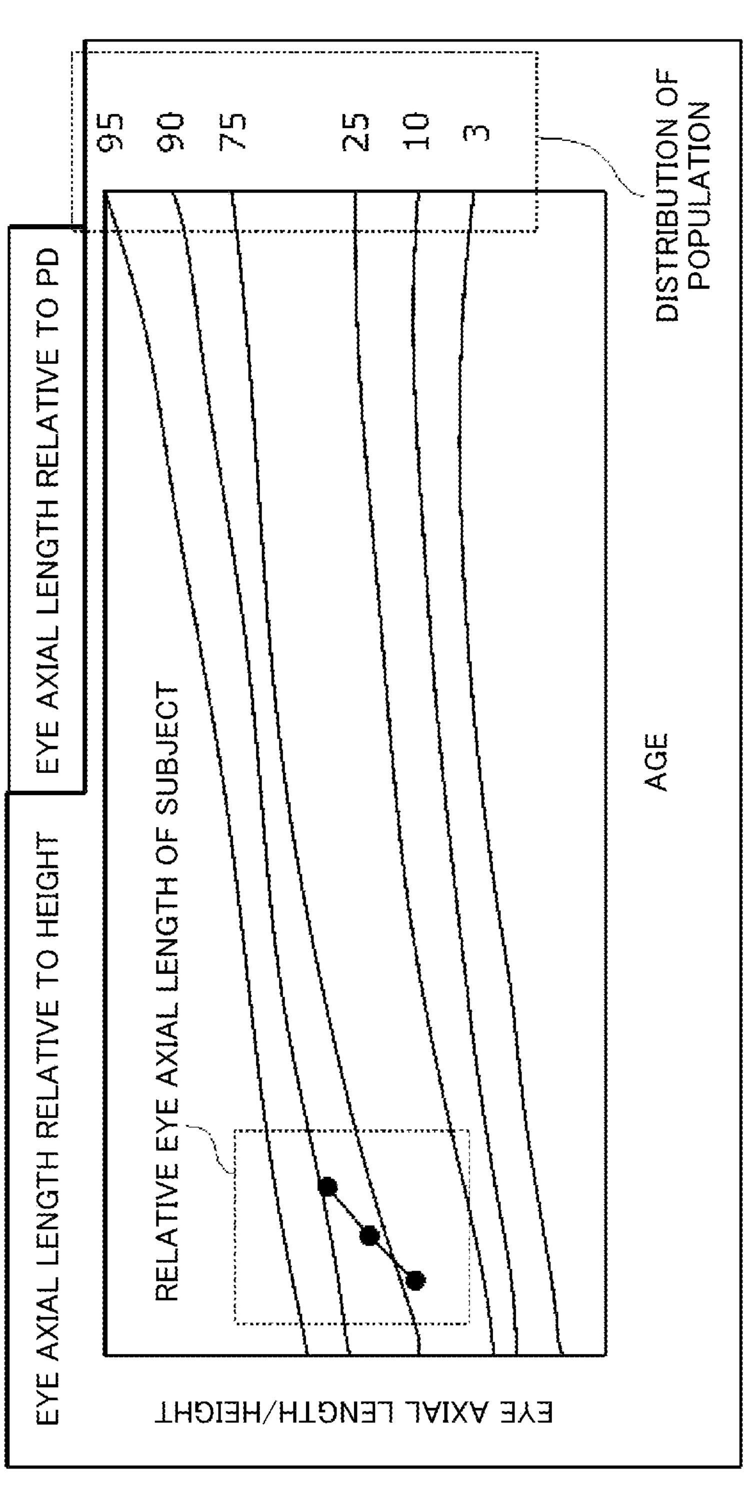
FIG. 4 shows an example of relative position information shown on the display of the terminal device.

FIG. 4 specifically shows the relative position information. FIG. 4 shows a screen that appears on the display 310 of the terminal device 300, for example. This screen shows the relative position information showing a comparison between the relative eye axial length of the subject calculated by the relative position information calculator 115 and the relative eye axial lengths included in the population in chronological order.

FIG. 4 shows a graph of the so-called percentile growth curves with age on the horizontal axis and the relative eye axial length, which is the value of eye axial length/height, on the vertical axis. On these curves, the transition of the relative eye axial length of the subject is plotted on the left part of the graph, and three measurement points and a line segment connecting them are shown. This plot is based on the fact that the relative eye axial length is associated with the timing of the measurement of the eye axial length. This time-series relative position information indicates that the relative eye axial length of the subject of this example increases every time the measurement was made. Thus, when the relative position information of the relative eye axial length shown in chronological order is used, the influence of individual growth is excluded and the progression of myopia compared with a group can be accurately checked. When two or more relative eye axial lengths of one subject measured at different timings are plotted, the progression indicating whether the subject's condition is more aggravated or improved as compared with the group can be understood more easily.

The relative position information is not limited to the above-described example. For example, the relative position information may be relative position information in which the relative eye axial length obtained through relativization using the corneal diameter is plotted on the horizontal axis and the relative eye axial length obtained through relativization using the corneal curvature is plotted on the vertical axis for analysis in four quadrants, or may be relative position information indicating chronological changes of these values.

Flow of Processing

Figure 5:
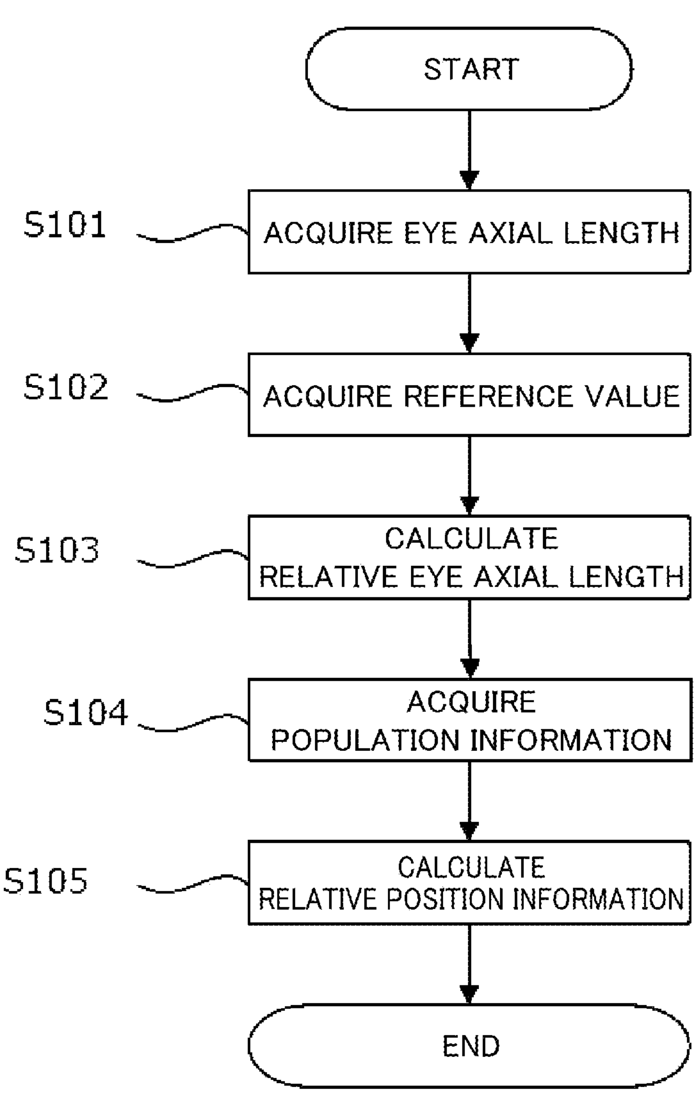
FIG. 5 shows a flowchart illustrating how myopia progression analysis of an embodiment of the present disclosure proceeds.

FIG. 5 shows a flowchart illustrating the flow of processing performed by the information management server 101 of the myopia progression analysis system 1000 of the embodiment of the present disclosure. A myopia progression analysis method will be described below with reference to the flowchart. This flowchart is an example, and the myopia progression analysis method is not limited to the processing of this flowchart.

In Step S101, the eye axial length acquisition section 111 acquires the eye axial length of the subject's eye.

In Step S102, the reference value acquisition section 112 acquires a numerical value related to the physical characteristics of the subject other than the eye axial length as the reference value.

In Step S103, the relative eye axial length calculator 113 calculates the relative eye axial length through relativization of the eye axial length acquired by the eye axial length acquisition section 111 using the reference value acquired by the reference value acquisition section 112.

In Step S104, the population information acquisition section 114 acquires population information which is a set of information about the relative eye axial lengths of a plurality of comparison targets to be compared with the subject.

In Step S105, the relative position information calculator 115 compares the relative eye axial length of the subject calculated by the relative eye axial length calculator 113 with the plurality of relative eye axial lengths included in the population information to calculate relative position information indicating the relative position of the relative eye axial length of the subject in a set of subjects.

As described above, the myopia progression analysis device, myopia progression analysis system, myopia progression analysis method, and myopia progression analysis program of the embodiment of the present disclosure can exclude the influence of individual growth and allow accurate check of the progression of axial myopia by the functions of: the eye axial length acquisition section 111 that acquires the eye axial length of the eye of the subject; the reference value acquisition section 112 that acquires a numerical value related to a physical characteristic of the subject other than the eye axial length as a reference value; the relative eye axial length calculator 113 that calculates a relative eye axial length through relativization of the eye axial length acquired by the eye axial length acquisition section 111 using the reference value acquired by the reference value acquisition section 112; the population information acquisition section 114 that acquires population information which is a set of information about the relative eye axial lengths of comparison targets to be compared with the subject; and the relative position information calculator 115 that compares the relative eye axial length of the subject calculated by the eye axial length calculator with the relative eye axial lengths of the plurality of comparison targets included in the population information to calculate relative position information indicating the relative position of the relative eye axial length of the subject in a set of comparison targets.

The relative eye axial length is associated with information about the timing of eye axial length measurement which is a basis for the calculation and information about the timing of reference value acquisition. The eye axial length and the reference value include timing when the information about the timing of eye axial length measurement corresponds to the information about the timing of reference value acquisition on a time-series basis. The relative position information calculator 115 calculates relative position information showing the relative eye axial length of the subject at predetermined measurement timing and the relative eye axial lengths of the plurality of comparison targets at corresponding measurement timing included in the population information in chronological order. This can exclude the influence of individual growth and allows accurate check of the progression of myopia compared with a group.

Using two or more relative eye axial lengths of the subject measured at different timings, the relative position information calculator 115 compares each of the relative eye axial lengths measured at the different timings with the relative eye axial lengths of the plurality of comparison targets included in the population information to calculate relative position information showing the relative position of the relative eye axial length of the subject in the set of comparison targets in chronological order. Thus, the progression indicating whether the subject's condition is more aggravated or improved as compared with the group can be understood more easily.

The physical characteristic of the subject used as the reference value is a physical characteristic related to the eye of the subject other than the eye axial length, and appropriately represents the eye-related physical characteristic of the subject when the physical characteristic is any one of a pupillary distance, corneal curvature, corneal diameter, or dioptric power of the subject. Thus, the characteristics of the eyeballs of the subject are acquired simultaneously with the eye axial length, allowing smooth analysis of the progression of myopia.

The physical characteristic of the subject used as the reference value is a physical characteristic related to a body part of the subject other than the eyes, and appropriately represents the characteristics of individual growth when the physical characteristic is any one of an eye socket size, height, or head size of the subject. This can exclude the influence of the individual growth, allowing accurate calculation of the relative eye axial length.

When the reference value used for the relativization to obtain the relative eye axial length includes a physical characteristic related to the eye of the subject other than the eye axial length and a physical characteristic related to a body part of the subject other than the eye, the relative eye axial length considering the physical characteristics more comprehensively can be obtained.

Program

Figure 6:
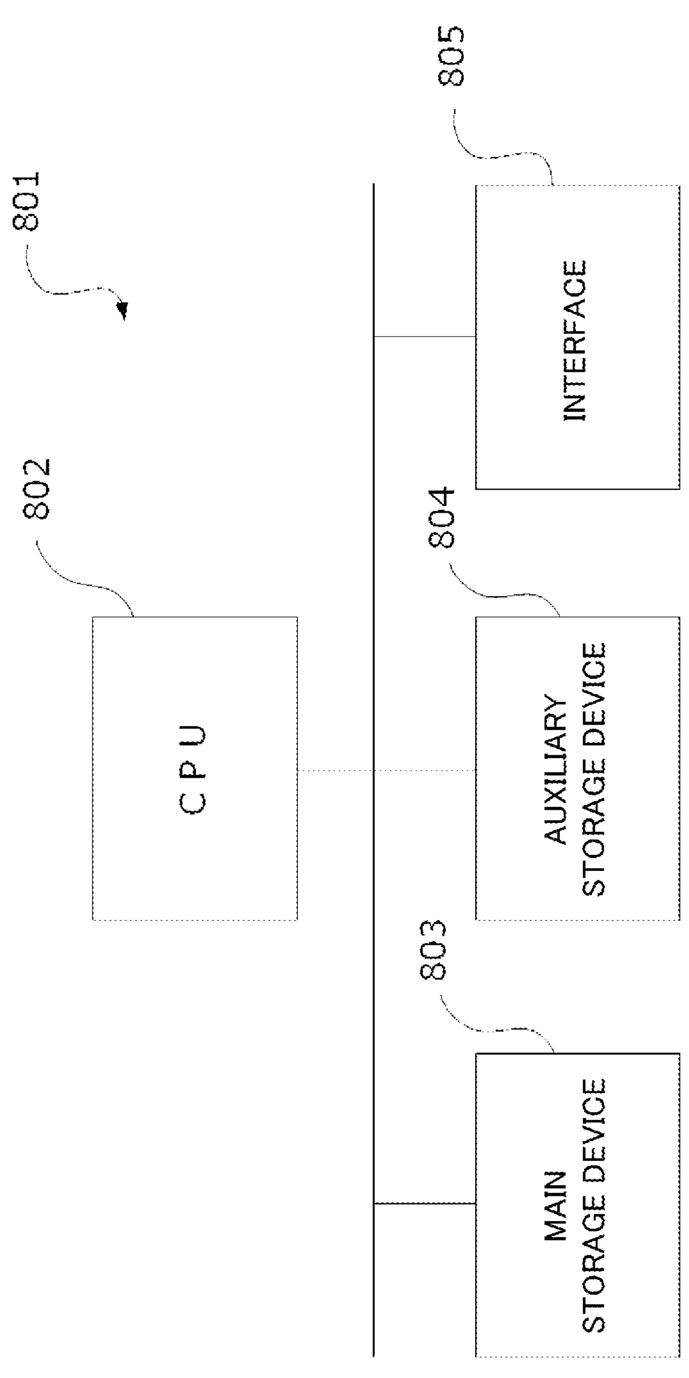
FIG. 6 is a schematic block diagram showing a configuration of a computer.

FIG. 6 is a schematic block diagram showing the configuration of a computer 801. The computer 801 includes a CPU 802, a main storage device 803, an auxiliary storage device 804, and an interface 805.

Details of a program that implements the functions constituting the information management server 101 of the embodiments will be described below.

The information management server 101 is implemented on the computer 801. The operation of the components of the information management server 101 is stored in the auxiliary storage device 804 in the form of a program. The CPU 802 reads out the program from the auxiliary storage device 804 and loads the program into the main storage device 803 to perform the above-described processing according to the program. Further, the CPU 802 reserves a storage region corresponding to the above-described storage in the main storage device 803 according to the program.

Specifically, the program is a myopia progression analysis program for analyzing the progression of myopia on the computer 801. The program achieves the function of acquiring an eye axial length of an eye of a subject, acquiring a numerical value related to a physical characteristic of the subject other than the eye axial length as a reference value, calculating a relative eye axial length through relativization of the eye axial length acquired by the eye axial length acquisition section using the reference value acquired by the reference value acquisition section, acquiring population information which is a set of information about relative eye axial lengths of a plurality of comparison targets to be compared with the subject, and comparing the relative eye axial length of the subject calculated by the relative eye axial length calculator with the plurality of relative eye axial lengths included in the population information to calculate relative position information indicating a relative position of the relative eye axial length of the subject in a set of subjects.

It should be noted that the auxiliary storage device 804 is an example of a non-transitory tangible medium. Other examples of the non-transitory tangible medium include a magnetic disk, a magneto-optical disk, a CD-ROM, a DVD-ROM, a semiconductor memory that are connected via the interface 805. When the program is distributed to the computer 801 via the network NW, the computer 801 that has received the distribution may load the program into the main storage device 803 to execute the processing.

The program may achieve some of the above-described functions. Further, the program may be a so-called differential file (differential program) that achieves the above-described functions in combination with another program already stored in the auxiliary storage device 804.

The embodiments of the present disclosure have been described above, but the aspects of the present disclosure are not limited to the embodiments.

DESCRIPTION OF REFERENCE CHARACTERS

101 Information Management Server
111 Eye Axial Length Acquisition Section
112 Reference Value Acquisition Section
113 Relative Eye Axial Length Calculator
114 Population Information Acquisition Section
115 Relative Position Information Calculator
121 Information Storage
200 Ophthalmologic Apparatus
210 Ophthalmologic Apparatus Processor
211 Ophthalmologic Apparatus Processor
212 Intraocular Distance Calculator
213 Eye Refractive Power Calculator
216 Ophthalmologic Apparatus Controller
221 Z Alignment System
222 XY Alignment System
230 Keratometry System
241 Refractometry Projection System
242 Refractometry Light-Receiving System
250 OCT Optical System
260 Fixation Projection System
270 Anterior Segment Observation System
291 Ophthalmologic Apparatus Moving Mechanism
292 Ophthalmologic Apparatus Communication Unit
293 Ophthalmologic Apparatus Display Unit
294 Ophthalmologic Apparatus Operation Unit
300 Terminal Device
310 Display
320 Input Unit
1000 Myopia Progression Analysis System
NW Network

The invention claimed is:

1. A myopia progression analysis device for analyzing progression of myopia of a subject, the myopia progression analysis device comprising:

a memory storing computer program instructions; and at least one processor configured to execute the computer program instructions, the computer program instructions configured to cause the at least one processor to perform operations of:

acquiring an eye axial length of an eye of the subject;

acquiring a numerical value related to a physical characteristic of the subject other than the eye axial length as a reference value;

calculating a relative eye axial length through relativization of the eye axial length using the reference value;

acquiring population information which is a set of information about relative eye axial lengths of a plurality of comparison targets to be compared with the subject; and comparing the relative eye axial length of the subject with the relative eye axial lengths of the plurality of comparison targets included in the population information to calculate relative position information indicating a relative position of the relative eye axial length of the subject in the set of comparison targets, wherein the physical characteristic of the subject used as the reference value is a physical characteristic related to a body part of the subject, and is any one of an eye socket size, height of the subject, or head size of the subject.

2. The myopia progression analysis device of claim 1, wherein the relative eye axial length is associated with information about timing of measurement of the eye axial length that is a basis for calculation and information about timing of acquisition of the reference value, the eye axial length and the reference value include timing when the information about the timing of measurement corresponds to the information about the timing of acquisition on a time-series basis, and comparing the relative eye axial length of the subject with the relative eye axial lengths of the plurality of comparison targets included in the population information comprises calculating the relative position information showing the relative eye axial length of the subject at predetermined measurement timing and the relative eye axial lengths of the plurality of comparison targets included in the population information at corresponding measurement timing in chronological order.

3. The myopia progression analysis device of claim 1, wherein comparing the relative eye axial length of the subject with the relative eye axial lengths of the plurality of comparison targets included in the population information comprises, using two or more relative eye axial lengths of the subject measured at different timings, comparing each of the relative eye axial lengths of the subject measured at the different timings with the relative eye axial lengths of the plurality of comparison targets included in the population information at corresponding measurement timing to calculate the relative position information showing the relative position of the relative eye axial length of the subject in the set of the comparison targets in chronological order.

4. The myopia progression analysis device of claim 1, wherein the reference value used for the relativization to obtain the relative eye axial length includes a physical characteristic related to the eye of the subject other than the eye axial length and the physical characteristic related to the body part of the subject other than the eye, and the physical characteristic related to the eye of the subject other than the eye axial length, and is any one of a pupillary distance, corneal curvature, corneal diameter, or dioptric power of the subject.

5. A myopia progression analysis system for analyzing progression of myopia of a subject, the myopia progression analysis system comprising:

a memory storing computer program instructions;

at least one processor configured to execute the computer program instructions, the computer program instructions configured to cause the at least one processor to perform operations of:

measuring an eye axial length of an eye of the subject;

acquiring the eye axial length;

acquiring a numerical value related to a physical characteristic of the subject other than the eye axial length as a reference value;

calculating a relative eye axial length through relativization of the eye axial length using the reference value;

acquiring population information which is a set of information about relative eye axial lengths of a plurality of comparison targets to be compared with the subject; and comparing the relative eye axial length of the subject with the relative eye axial lengths of the plurality of comparison targets included in the population information to calculate relative position information indicating a relative position of the relative eye axial length of the subject in the set of comparison targets, wherein the physical characteristic of the subject used as the reference value is a physical characteristic related to a body part of the subject, and is any one of an eye socket size, height of the subject, or head size of the subject.

6. The myopia progression analysis system of claim 5, wherein the reference value used for the relativization to obtain the relative eye axial length includes a physical characteristic related to the eye of the subject other than the eye axial length and the physical characteristic related to the body part of the subject other than the eye, and the physical characteristic of the subject used as the reference value is a physical characteristic related to the eye of the subject other than the eye axial length, and is any one of a pupillary distance, corneal curvature, corneal diameter, or dioptric power of the subject.

7. A myopia progression analysis method for analyzing progression of myopia of a subject, the myopia progression analysis method comprising:

acquiring an eye axial length of an eye of the subject;

acquiring a numerical value related to a physical characteristic of the subject other than the eye axial length as a reference value;

calculating a relative eye axial length through relativization of the eye axial length using the reference value;

acquiring population information which is a set of information about relative eye axial lengths of a plurality of comparison targets to be compared with the subject; and comparing the relative eye axial length of the subject with the relative eye axial lengths of the plurality of comparison targets included in the population information to calculate relative position information indicating a relative position of the relative eye axial length of the subject in the set of comparison targets, wherein the physical characteristic of the subject used as the reference value is a physical characteristic related to a body part of the subject, and is any one of an eye socket size, height of the subject, or head size of the subject.

8. A myopia progression analysis program for analyzing progression of myopia of a subject, the program causing a computer to execute:

acquiring an eye axial length of an eye of the subject;

acquiring a numerical value related to a physical characteristic of the subject other than the eye axial length as a reference value;

calculating a relative eye axial length through relativization of the eye axial length using the reference value;

acquiring population information which is a set of information about relative eye axial lengths of a plurality of comparison targets to be compared with the subject; and comparing the relative eye axial length of the subject with the relative eye axial lengths of the plurality of comparison targets included in the population information to calculate relative position information indicating a relative position of the relative eye axial length of the subject in the set of comparison targets, wherein the physical characteristic of the subject used as the reference value is a physical characteristic related to a body part of the subject, and is any one of an eye socket size, height of the subject, or head size of the subject.

* * * * *